US00PP25598P3

(12) United States Plant Patent
Deng et al.

(10) Patent No.: US PP25,598 P3
(45) Date of Patent: May 26, 2015

(54) *CALADIUM* PLANT NAMED 'UF 4424'

(50) Latin Name: *Caladium×hortulanum*
Varietal Denomination: UF 4424

(71) Applicants: Zhanao Deng, Riverview, FL (US); Brent K. Harbaugh, Bradenton, FL (US)

(72) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 229 days.

(21) Appl. No.: 13/815,705

(22) Filed: Mar. 14, 2013

(65) Prior Publication Data

US 2014/0283266 P1 Sep. 18, 2014

(51) Int. Cl.
*A01H 5/12* (2006.01)
*A01H 5/02* (2006.01)

(52) U.S. Cl.
CPC ..... *A01H 5/02* (2013.01)
USPC ..... Plt./373

(58) Field of Classification Search
USPC ..... Plt./373
See application file for complete search history.

*Primary Examiner* — Anne Grunberg
(74) *Attorney, Agent, or Firm* — Christopher & Weisberg, P.A.

(57) ABSTRACT

A new and distinct cultivar of *Caladium* plant named 'UF 4424', characterized by its mounding, dense bushy growth habit, broad lanceolate leaves that have bright red, waxy center and undulate margins, and plants that are sunburn-tolerant and attractive in containers or landscapes.

7 Drawing Sheets

STATEMENT REGARDING FEDERALLY SPONSORED RESEARCH OR DEVELOPMENT

This invention was made with government support under FLA-BRA-04162 awarded by the Cooperative State Research, Education, and Extension Service, USDA. The government has certain rights in the invention.

Latin name: *Caladium×hortulanum.*
Cultivar denomination: 'UF 4424'.

CROSS-REFERENCE TO RELATED APPLICATION n/a

BACKGROUND OF THE NEW CULTIVAR

The present invention relates to a new and distinct cultivar of *Caladium* plant, botanically known as *Caladium×hortulanum,* commercially referred to as a strap leaf-type or lance leaf-type *caladium* and hereinafter referred to by the name 'UF 4424'.

*Caladiums* (also referred to as *Caladium* plants) are ornamental aroids frequently used as pot and landscape plants for their colorful foliage and ease of growing. The objective of the Inventors' breeding program is to create new *Caladium* cultivars that have compact growth habit, numerous leaves, attractive foliage, and exceptional container and landscape performance.

*Caladium* cultivar 'UF 4424' originated from a cross between 'Florida Sweetheart' (U.S. Plant Pat. No. 8,526) and 'Red Flash' (commercial cultivar, not patented) that was made in Bradenton, Fla., in spring 2004. The new *Caladium* cultivar 'UF 4424' was discovered and selected by the inventors as a single plant in Wimauma, Fla., in winter 2005. The

*Caladium* cultivar 'UF 4424' has been found to retain its distinctive characteristics through at least seven generations of successive asexual propagations conducted in Wimauma, Fla., via tuber divisions since April of 2006.

Plant Breeder's Rights for this cultivar have not been applied for. 'UF 4424' has not been made publicly available more than one year prior to the filing of this application.

SUMMARY OF THE INVENTION

The new *Caladium* cultivar has not been observed under all possible environmental conditions. The phenotype may vary somewhat with variations in environment such as temperature, light intensity, water status, fertilizer rate and type, without, however, any variance in genotype.

The following are the most outstanding and distinguishing characteristics of this new *Caladium* cultivar when grown under (normal or standard) horticultural practices in Wimauma, Fla. The combination of these characteristics distinguishes 'UF 4424' as a new and distinct cultivar of *Caladium:*

1. Symmetrical, outwardly arching and rounded plant form;
2. Mounding, dense and bushy growth habit;
3. Broad lance-type leaves;
4. Large bright red and waxy center on leaves; and
5. Sunburn-tolerant and attractive plants in containers or sunny or shady landscapes.

The new *Caladium* cultivar 'UF 4424' differs from its female parent, 'Florida Sweetheart' (U.S. Plant Pat. No. 8,526), in the following characteristics:

1. Plants of 'UF 4424' are taller than plants of 'Florida Sweetheart';
2. Leaves of 'UF 4424' are longer than the leaves of 'Florida Sweetheart';

3. Leaves of 'UF 4424' are more elongated than the leaves of 'Florida Sweetheart';
4. Leaves of 'UF 4424' have a large red center, whereas leaves of 'Florida Sweetheart' have a light rose center; and
5. Leaves of 'UF 4424' are highly waxy, whereas leaves of 'Florida Sweetheart' are not waxy.

The new *Caladium* cultivar 'UF 4424' differs from its male parent, 'Red Flash', in the following characteristics:

1. Plants of 'UF 4424' are shorter than plants of 'Red Flash';
2. Leaves of 'UF 4424' are of a lance type, whereas leaves of 'Red Flash' are of a fancy type;
3. Leaves of 'UF 4424' are significantly smaller than leaves of 'Red Flash';
4. Petioles of 'UF 4424' attach to the base of leaves, whereas petioles of 'Red Flash' attach to the lower back of the leaves; and
5. Leaves of 'UF 4424' are non-spotted, whereas leaves of 'Red Flash' have many spots.

The new *Caladium* cultivar 'UF 4424' can also be compared to the cultivar 'Florida Red Ruffles', disclosed in U.S. Plant Pat. No. 13,136. In side-by-side comparisons conducted in Wimauma, Fla., plants of the new *Caladium* cultivar differed from plants of 'Florida Red Ruffles' in the following characteristics:

1. Plants of 'UF 4424' were taller and wide than plants of 'Florida Red Ruffles';
2. Leaves of 'UF 4424' were longer and wider than leaves of 'Florida Red Ruffles';
3. Leaves of 'UF 4424' had a bright red center, whereas leaves of 'Florida Red Ruffles' had a dark red center; and
4. Leaves of 'UF 4424' were waxier than leaves of 'Florida Red Ruffles'.

The new *Caladium* cultivar 'UF 4424' can also be compared to the *Caladium* cultivar 'UF 44-4', disclosed in U.S. Plant Pat. No. 24,680. In side-by-side comparisons conducted in Wimauma, Fla., plants of the new *Caladium* cultivar 'UF 4424' differed from plants of 'UF 44-4' in the following characteristics:

1. Plants of 'UF 4424' were more elongated, whereas leaves of 'UF 44-4' were more rounded;
2. Leaves of 'UF 4424' had a bright red center, whereas 'UF 44-4' had a red-purple center;
3. Leaves of 'UF 4424' were waxier than leaves of 'UF 44-4' were;
4. Petioles of 'UF 4424' were longer and sturdier than petioles of 'UF 44-4'; and
5. Plants of 'UF 4424' were taller and wider than plants of 'UF 44-4'.

The new *Caladium* cultivar 'UF 4424' can also be compared to the *Caladium* cultivar 'UF 4412', disclosed in co-pending U.S. application Ser. No. 13/815,693. In side-by-side comparisons conducted in Wimauma, Fla., plants of 'UF 4424' differed from plants of 'UF 4412' in the following characteristics:

1. Leaves of 'UF 4424' were lanceolate with an elongated acute apex while leaves of 'UF 4412' were heart-shaped;
2. Margins of the leaves of 'UF 4424' were more undulate than margins of the leaves of 'UF 4412';
3. Leaves of 'UF 4424' lacked noticeable netted veins while leaves of 'UF 4412' had netted greyed-purple secondary veins; and
4. Leaves of 'UF 4424' were highly waxy, whereas leaves of 'UF 4412' were not waxy.

DESCRIPTION OF THE FIGURES

The accompanying photographs (as shown in FIGS. 1-7) illustrate the overall appearance of the new *Caladium* cultivar. These photographs show the colors as true as can be reasonably obtained in colored reproductions of this type. Colors in the photographs may differ slightly from the color values cited in the detailed botanical description, which accurately describe the colors of the new *Caladium* cultivar.

DESCRIPTION OF THE NEW CULTIVAR

Figure 1:
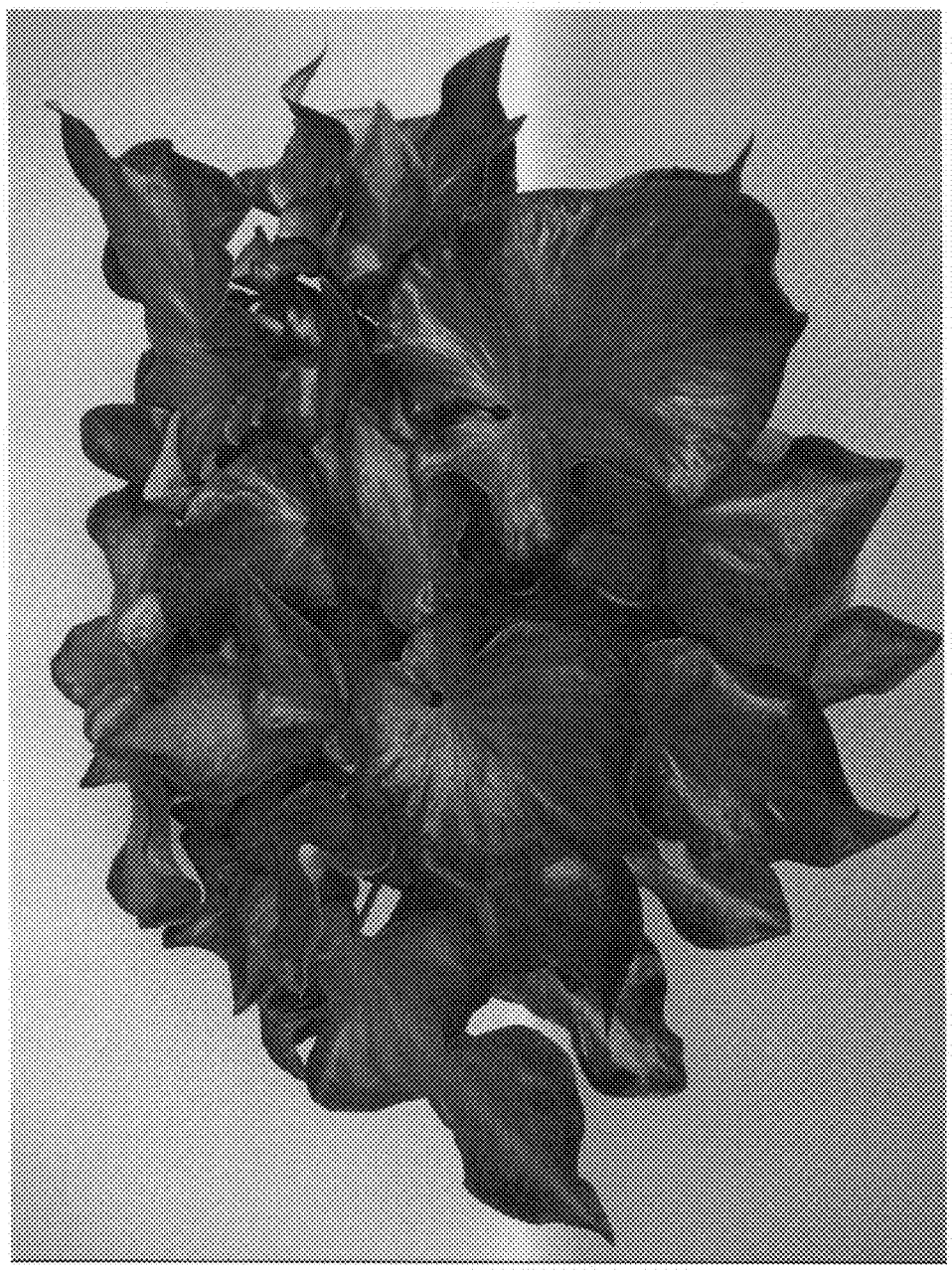
FIG. 1 shows a photograph of a side view of a typical plant of the new *Caladium* cultivar 'UF 4424' grown in a 20-cm diameter container in a shadehouse.
Figure 2:
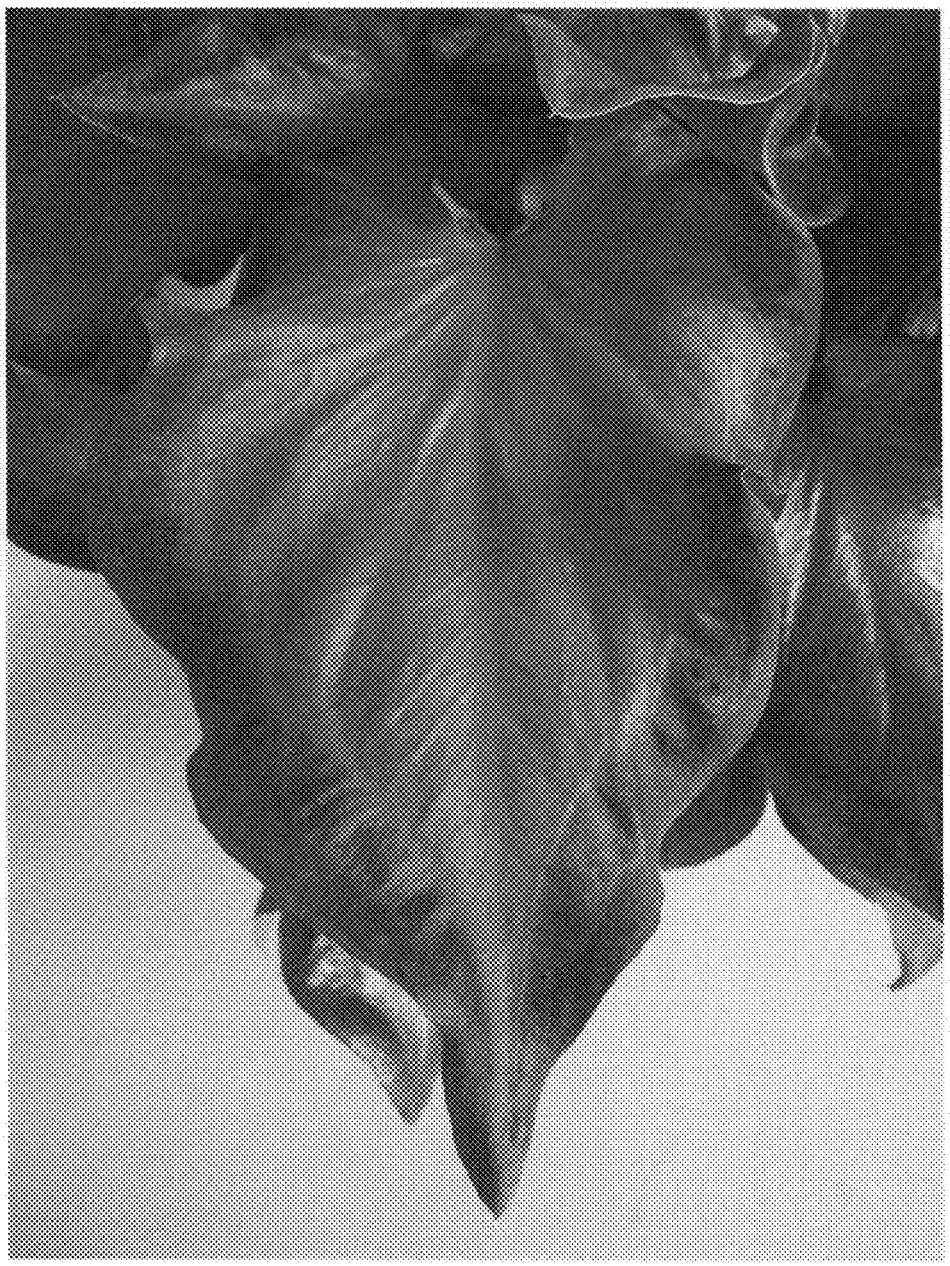
FIG. 2 shows a photograph of a top view of a typical leaf of the new *Caladium* cultivar 'UF 4424' grown in a 20-cm diameter container in a shadehouse.
Figure 3:
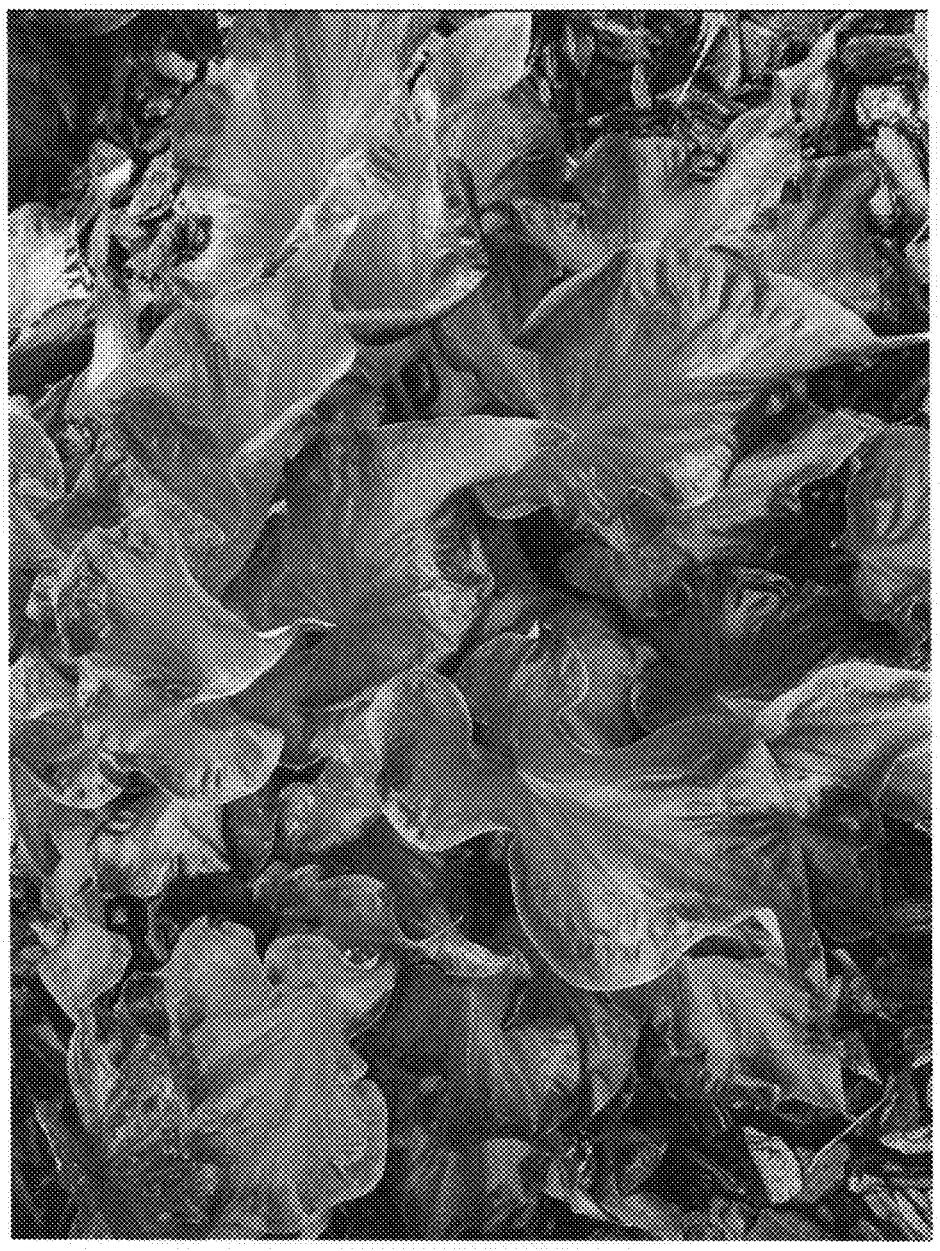
FIG. 3 shows a photograph of a top view of typical plants of the new *Caladium* cultivar 'UF 4424' grown in an outdoor nursery.
Figure 4:
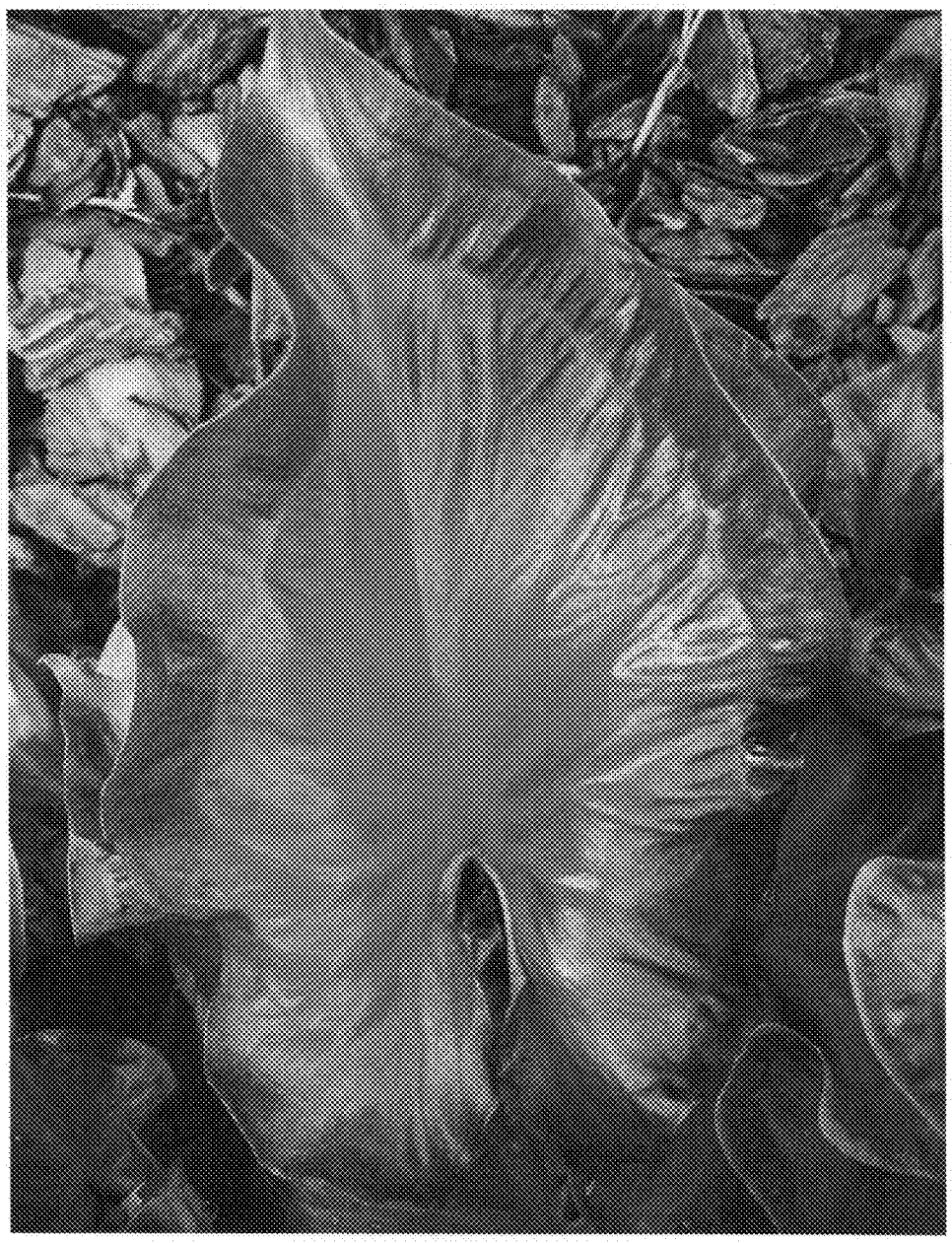
FIG. 4 shows a photograph of a top view of a typical leaf of the new *Caladium* cultivar 'UF 4424' grown in an outdoor nursery.
Figure 5:
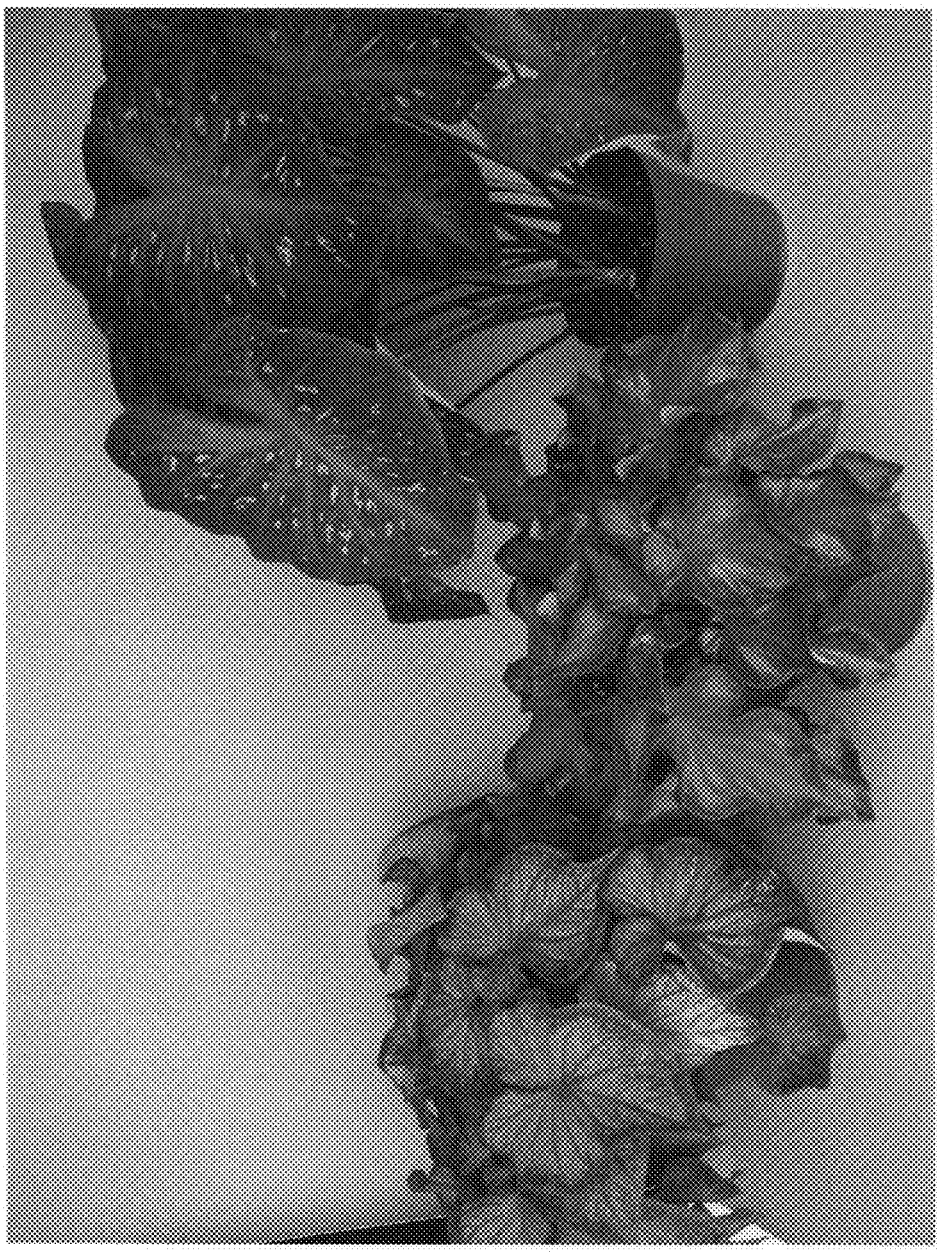
FIG. 5 shows a photograph of a side view of typical plants of 'Florida Sweetheart' (left), 'UF 4424' (center) and 'Red Flash' (right) grown in 20-cm diameter container in a shadehouse.
Figure 6:
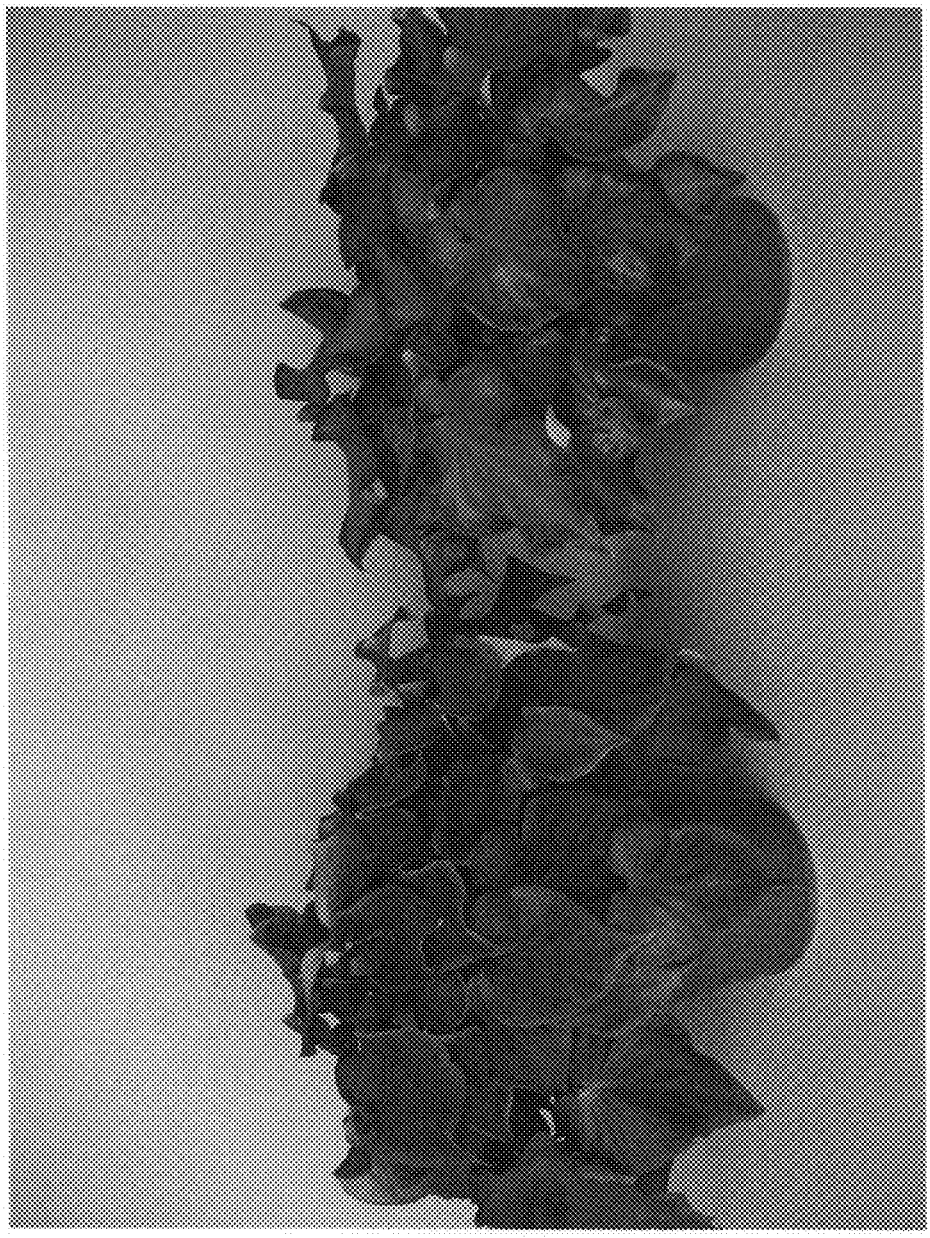
FIG. 6 shows a photograph of a side view of typical plants of 'Florida Red Ruffles' (left) and 'UF 4424' (right) grown in 20-cm diameter container in a shadehouse.
Figure 7:
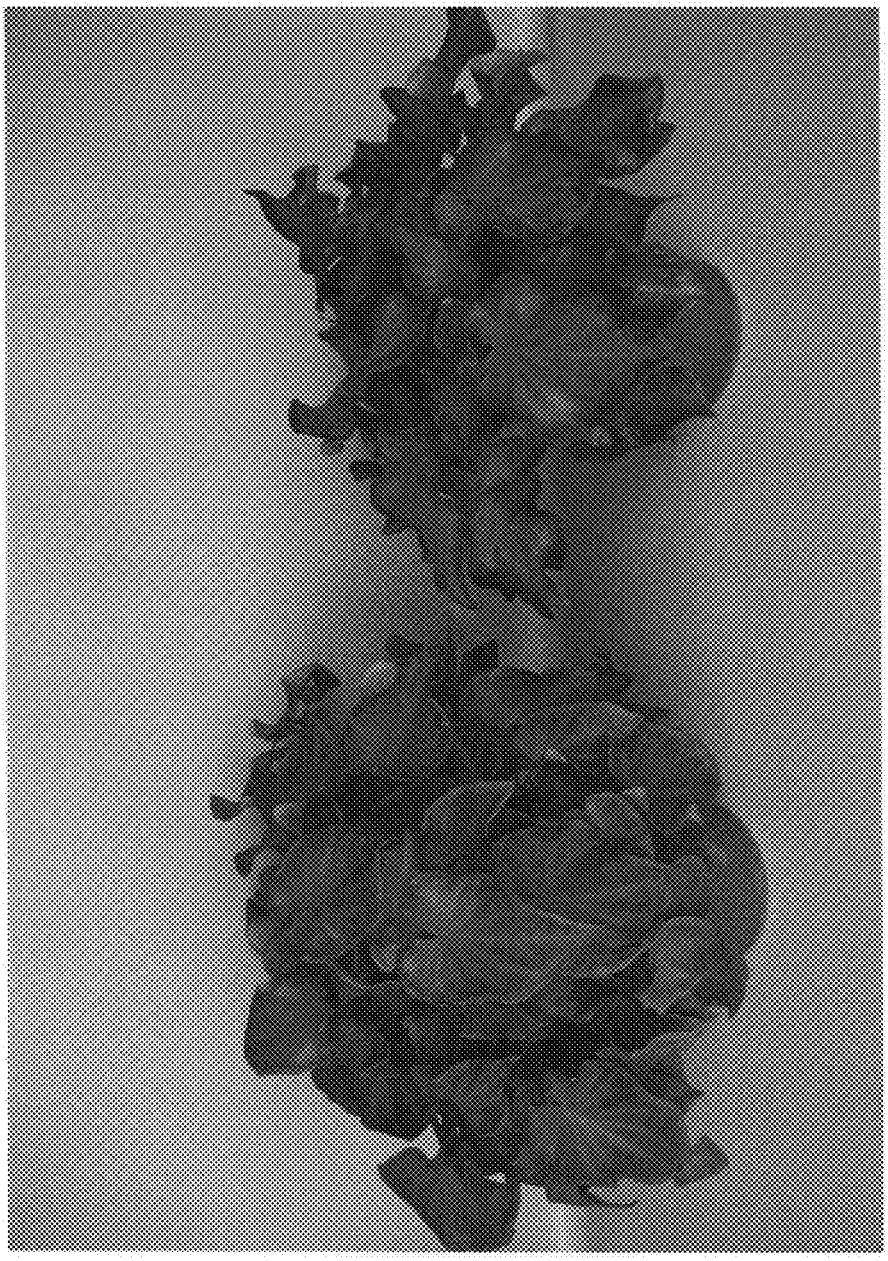
FIG. 7 shows a photograph of a side view of typical plants of 'UF 44-4' (left) and 'UF 4424' (right) grown in 20-cm diameter container in a shadehouse.

In the following description, color references are made to The Royal Horticultural Society Colour Chart, 1986 Edition, except where general terms of ordinary dictionary significance are used. The features of 'UF 4424' described herein are shown in FIGS. 1-7.

Description of Growing Conditions

The following observations and measurements describe plants grown in 20-cm containers in Wimauma, Fla., during the summer in a polypropylene-covered shadehouse and plants grown in ground beds in Wimauma, Fla., during the late summer in an outdoor nursery. All plants were grown under conditions and practices similar to those generally used in commercial *Caladium* production.

During the production of the plants, day temperatures ranged from approximately 23.5° C. to 34.4° C., night temperatures ranged from approximately 20.5° C. to 23.5° C., and light levels were approximately 944 foot-candles in the shadehouse and 9744 foot-candles in the outdoor nursery. Plants grown in the shadehouse were approximately seven weeks from planting tubers when the photographs and the detailed description were taken. Plants grown in the outdoor nursery were approximately three months from planting tuber pieces when the photographs and the detailed description were taken.

Botanical Description

Botanical classification:

*Family.*—Araceae.

*Botanical name.*—*Caladium×hortulanum.*

*Common name.*—*Caladium.*

*Cultivar.*—'UF 4424' (*Caladium×hortulanum* cultivar UF 4424).

Parentage:

*Female or seed parent.*—'Florida Sweetheart' (U.S. Plant Pat. No. 8,526).

*Male or pollen parent.*—'Red Flash', not patented.

Propagation:

*Type.*—By tubers and by tuber divisions.

*Time to initiate roots, summer.*—Approximately seven to ten days at 32° C.

*Time to initiate roots, winter.*—Approximately two to three weeks at 24° C.

Tuber description: Jumbo-sized (6.4 to 8.9 cm in diameter) tubers are multi-segmented, bearing six to eight dominant buds.

*Height of tubers.*—2 to 5 cm.

*Diameter of tubers.*—Up to 9 cm.

*Texture.*—Thick, starchy; slightly brittle.

*Color.*—Epidermis, Close to brown (RHS 200D); Interior, yellow (RHS 12B).

*Root description.*—Dense, thick and white fleshy roots.

Plant description:

*Type.*—Herbaceous perennial.

*Plant form.*—Upright, outwardly arching and symmetrical plant.

*Growth habit.*—Compact and mounding, dense foliage, suitable for 10.0 cm to 25.0-cm containers. Leaf petioles arising from tubers; petioles mostly semi-upright and curving outwardly with development.

*Plant height, from soil level to top of leaf plane, shadehouse-grown plants.*—Approximately 39 cm.

*Plant height, from soil level to top of inflorescences, shadehouse-grown plants.*—Approximately 40 cm.

*Plant spread, shadehouse-grown plants.*—Approximately 67 cm×62 cm.

*Plant height, from soil level to top of leaf plane, outdoor nursery-grown plants.*—Approximately 40 cm.

*Plant height, from soil level to top of inflorescences, outdoor nursery-grown plants.*—Inflorescences not observed.

*Plant spread, outdoor nursery-grown plants.*—Approximately 80 cm×72 cm.

Foliage description (shadehouse-grown and outdoor-grown):

*Length, shadehouse-grown plants.*—Approximately 20 cm.

*Width, shadehouse-grown plants* (*flattened*).—Approximately 13 cm.

*Length, outdoor nursery-grown plants.*—Approximately 24 cm.

*Width, outdoor nursery-grown plants* (*flattened*).—Approximately 14.5 cm.

*Shape.*—Ovate.

*Apex.*—Acuminate to acute.

*Base.*—Cordate.

*Margin.*—Entire; moderately undulate.

*Texture, upper surface.*—Smooth, glabrous.

*Texture, lower surface.*—Smooth, glabrous, glaucous.

*Venation pattern.*—Pinnate.

Leaf color, shadehouse-grown plants:

*Developing and fully expanded leaves.*—Upper surface: Center: Close to red (RHS 53A and 53B). Border and margins: Close to green (RHS 139A). Venation: Midrib and primary veins: Close to red (RHS 53A). Lower surface: Center: Close to greyed-purple (RHS 187C). Border and margins: Close to greyed-green (RHS 191A). Venation: Midrib and primary veins: Close to greyed-purple (RHS 187C).

Leaf color, outdoor nursery-grown plants:

*Developing leaves.*—Upper surface: Center: Close to red (RHS 53A). Border and margins: Close to green (RHS 139A). Venation: Midrib and primary veins: Close to red (RHS 53A). Lower surface: Center: Greyed-purple (RHS 187C). Border and margins: Close to greyed-green (RHS 191A and 191B). Venation: Midrib and primary veins: Close to greyed-purple (RHS 187C).

*Fully expanded leaves.*—Upper Surface: Center: Close to red-purple (RHS 60A) with blotches of green (RHS 137A) near the borders. Border and margins: Close to green (RHS 137A). Venation: Midrib and primary veins: Close to red (RHS 53B). Lower surface: Center: Close to greyed-purple (RHS 185B). Border and margins: Close to greyed-green (RHS 191A). Venation: Midrib, Close to greyed-purple (RHS 185B). Primary vein, greyed-red (RHS 182D, but lighter).

Petiole:

*Aspect.*—Mostly erect, curving outwardly with development.

*Length, shadehouse-grown plants.*—Approximately 19.5 to 32.5 cm.

*Diameter, distal, shadehouse-grown plants.*—Approximately 4.5 mm.

*Diameter, proximal, shadehouse-grown plants.*—Approximately 6.9 mm.

*Length, outdoor nursery-grown plants.*—Approximately 26.0 cm to 32.0 cm.

*Diameter, distal, outdoor nursery-grown plants.*—Approximately 4.8 mm.

*Diameter, proximal, outdoor nursery-grown plants.*—Approximately 7.3 mm.

*Strength.*—Strong; flexible.

*Color, shadehouse-grown plants.*—Close to greyed-red (RHS 182B to 182D) with blotches of brown (RHS 200A) or greyed-purple (RHS 185C) with blotches of black (RHS 202A).

*Color, proximal, outdoor nursery-grown plants.*—Close to greyed-red (RHS 181C) with dashes of brown (RHS 200C and 200D).

*Wing length, shadehouse-grown plants.*—Approximately 2.5 cm to 7.5 cm.

*Wing diameter, shadehouse-grown plants.*—Approximately 3.9 mm to 8.3 mm.

*Wing length, outdoor nursery-grown plants.*—Approximately 3.0 cm to 4.5 cm.

*Wing diameter, outdoor nursery-grown plants.*—Approximately 5.4 mm to 6.9 mm.

*Wing color, shadehouse-grown plants.*—Close to greyed-red (RHS 182D, but lighter) with streaks of brown (RHS 200A).

*Wing color, outdoor nursery-grown plants.*—Close to greyed-red (RHS 182D, but lighter) with small streaks of brown (RHS 200C).

Inflorescence description:

*Inflorescence arrangement.*—Upright hooded spathes surrounding a columnar spadix borne on an upright scape. Spadix carries sessile, simple female and male flowers separated into two zones. Female flowers arranged on the lower one-third of the spadix; male flowers arranged on the upper two-thirds of the spadix. Sterile flowers develop between female and male flower zones. Spadix constricts near the sterile flower zone.

*Fragrance.*—None detected.

*Natural flowering season/longevity.*—Plants of 'UF 4424' typically flower during spring or early summer in central Florida. Flowers develop about seven weeks after growth commence. Inflorescences last about four days before fading.

*Spathe*.—Length: Approximately 14.5 cm. Width, distal: Approximately 3.5 cm. Width, proximal.—Approximately 2.7 cm. Shape: Ovate to somewhat obovate. Apex: Acute to acuminate. Base: Tapering. Margin: Entire. Texture, upper and lower surfaces: Smooth, glabrous. Color: Front surface: Upper two-thirds: Close to white (RHS 155A). Lower one-third: Close to greyed-green (RHS 193A) with large blotches of red-purple (RHS 60C and 60D). Rear surface: Upper two-thirds: Close to yellow-green (RHS 145C) with streaks of yellow-green (RHS 144A) and white (RHS 155A). Lower one-third: Close to greyed-green (RHS 193A) with large blotches of red-purple (RHS 60C).

*Spadix*.—Length, entire spadix: Approximately 9.4 cm. Length, male flower zone: Approximately 5.4 cm. Length, sterile flower zone: Approximately 2.2 cm. Length, female flower zone: Approximately 2.0 cm. Diameter, male flower zone: Approximately 8.3 mm. Diameter, sterile flower zone: Approximately 6.3 mm. Diameter, female flower zone: Approximately 1.0 cm. Shape: Spindle-shaped to columnar. Apex: Obtuse. Base: Obtuse. Aspect: Upright. Color, mature, male zone: Close to yellow-white (RHS 158C). Color, mature, sterile zone: Close to yellow-white (RHS 158B). Color, mature, female zone: Close to yellow (RHS 10B). Male flowers: Quantity per spadix: Approximately 142. Shape: Obovate. Height: Approximately 2.0 mm. Diameter: Approximately 3.6 mm. Anther color: Close to green-white (RHS 157D). Amount of pollen: none observed. Female flowers: Quantity per spadix: Approximately 123. Shape: Obovate. Height: Approximately 2.0 mm. Diameter: Approximately 1.5 mm. Stigma color: Close to greyed-orange (RHS 164C). Ovary color: Close to white (RHS 155D).

*Scape*.—Length: Approximately 22.8 cm. Diameter: Approximately 7.0 mm. Strength: Very sturdy. Aspect: Erect. Texture: Smooth, glabrous, glaucous. Color, proximal: Close to greyed-red (RHS 182C to 182D) with blotches of brown (RHS 200A to 200B). Just below spathe: Close to green (RHS 139D).

*Seed and fruit*.—Seed and fruit development has not been observed.

Disease/pest resistance: Plants of 'UF 4424' have been observed to be resistant to *Xanthomonas* leaf spot.

Temperature tolerance: Tolerant to temperatures ranging from approximately 7° C. to approximately 40° C.

Sunburn tolerance: Plants of 'UF 4424' have been observed to be tolerance to sunburns.

Comparison with Known Cultivars

The new *Caladium* cultivar 'UF 4424' was evaluated for tuber production at the Gulf Coast Research and Education Center in Wimauma, Fla. in 2009 and 2010. The soil was EauGallie fine sand with about 1% organic matter and pH values between 6.2 and 7.4. *Caladium* plants were grown in the field using a plastic-mulched raised-bed system. In 2009, field beds (81 cm wide, 20 cm high) were fumigated on 27 February with a mixture of 50% methyl bromide and 50% chloropicrin (by volume) at the rate of 196 $kg \cdot ha^{-1}$. *Caladium* seed pieces (tuber pieces, approximately 2.5×2.5×2.5 cm) were manually planted 9 April at approximately 15-cm spacing between rows and in rows. Drip tapes were buried under the plastic mulch and delivered approximately 6 mm of water to the bed per day. Fertigation (through the drip irrigation system) began when young *Caladium* plants emerged from the soil, supplying 6N-0.8P-3.9K soluble fertilizer at the rate of approximately 1.9 kg of $nitrogen \cdot ha^{-1} \cdot day^{-1}$ and a total 290 kg of $nitrogen \cdot ha^{-1}$ per growing season. One additional teaspoon (approximately seven grams) of the controlled-release fertilizer Osmocote® (15N-2.6P-10K, 5-6 months; Scotts Co., Marysville, Ohio) was applied to each plant on 21 July. Tubers were dug from the soil on 30 November to 2 Dec. 2009. Tuber grading was by the maximum diameter: Supper Mammoth (greater than 11.4 cm), Mammoth (8.9 to 11.4 cm), Jumbo (6.4 to 8.9 cm), No. 1 (3.8 to 6.4 cm), and No. 2 (2.5 to 3.8 cm). Tuber grades and counts were converted into a Production Index (PI) to show the relative economic value of the harvested tubers per field plot: PI=8n (Supper Mammoth)+6n (Mammoth)+4n (Jumbo)+2n (No. 1)+n (No. 2), where n=number of tubers in the grade.

In 2010, ground beds (91 cm wide, 20 cm high) were fumigated on 21 March with PIC-Clor® 60 (39% 1,3-dichloropropene and 59.6% chloropicrin; Soil Chemicals Corp., Hollister, Calif.) at the rate of 426 $kg \cdot ha^{-1}$. *Caladium* seed pieces were planted on 9 April with 15-cm spacing between and in rows. A seepage irrigation system was used to maintain a water table below the *caladium* root system. Approximately 14 grams of Osmocote® 15N-2.6P-10K (8-9 months) was applied to each plant on 18 May and again on 13 August. *Caladium* tubers were dug from the soil on 3-6 December. Tuber grading was conducted as above described.

In each growing season, field plots were arranged in a randomized complete block fashion with three blocks, and each plot was 1.2 $m^2$ and was planted with 30 *caladium* seed pieces. 'Florida Red Ruffles' and 'Florida Sweetheart' were included in each block. Analyses of variance were conducted using the PROC GLM procedure in SAS (SAS Institute, Cary, N.C.) to compare the tuber yield of 'UF 4424' to that of 'Florida Red Ruffles', 'Florida Sweetheart' and 'UF 4412'.

Table 1 shows the tuber weight, marketable tubers, production index, and grade distribution of 'UF 4424' grown in Wimauma, Fla., in 2009 and 2010. Values presented for each year are means of three plots in three randomized complete blocks.

TABLE 1

| | Tuber | | | Tuber distribution (%) | | | | |
|---|---|---|---|---|---|---|---|---|
| Cultivars | Weight (kg) | Production index | Marketable (no.) | Super mammoth | Mammoth | Jumbo | No. 1 | No. 2 |
| | Year 2009 | | | | | | | |
| 'UF 4424' | 3.4 a | 135 a | 61.0 b | | 4.0 | 14.8 ab | 58.3 | 22.9 |
| 'Florida Red Ruffles' | 1.8 b | 72 b | 44.7 c | | | 4.4 c | 48.8 | 46.8 |

TABLE 1-continued

| Cultivars | Tuber Weight (kg) | Tuber Production index | Tuber Marketable (no.) | Tuber distribution (%) Super mammoth | Mammoth | Jumbo | No. 1 | No. 2 |
|---|---|---|---|---|---|---|---|---|
| 'Florida Sweetheart' | 3.9 a | 136 a | 67.3 ab | | 1.3 | 19.5 a | 38.9 | 40.3 |
| 'UF 4412' | 3.6 a | 146 a | 76.7 a | | 1.9 | 7.5 bc | 65.3 | 25.4 |
| LSD ($\alpha$ = 0.05) | 1.16 | 23.4 | 14.5 | | NS | 10.0 | NS | NS |
| | Year 2010 | | | | | | | |
| 'UF 4424' | 2.4 | 108 | 44.3 | | 6.8 | 21.3 | 45.0 ab | 26.9 |
| 'Florida Red Ruffles' | 1.9 | 109 | 40.3 | | 2.4 | 41.1 | 36.7 ab | 19.9 |
| 'Florida Sweetheart' | 2.9 | 129 | 45.0 | | 9.2 | 42.4 | 20.8 b | 27.6 |
| 'UF 4412' | 2.5 | 113 | 47.0 | | 4.7 | 19.2 | 56.1 a | 20.0 |
| LSD ($\alpha$ = 0.05) | NS | NS | NS | | NS | NS | 29.1 | NS |

[z]mean values with the same letter within columns are not significantly different at P ≤ 0.05.
LSD: least significant difference; NS: not significantly different at P ≤ 0.05.

As shown in Table 1, 'UF 4424' was as productive as 'Florida Sweetheart' in both 2009 and 2010 growing seasons. The two cultivars produced similar amounts of tubers (3.4 kg and 3.9 kg) in 2009 and in 2010 (2.4 kg and 2.9 kg), similar numbers of marketable tubers in 2009 (61.0 and 67.3) and in 2010 (44.3 and 45.0), and a similar PI in 2009 (135 and 136) and in 2010 (108 and 129).

As shown in Table 1, 'UF 4424' was more productive than 'Florida Red Ruffles' in 2009 and as productive as 'Florida Red Ruffles' in 2010. In the 2009 growing season, 'UF 4424' produced a greater amount of tubers (3.4 kg vs. 1.8 kg), a larger number of marketable tubers (61.0 vs. 44.7), and a higher PI (135 vs. 72). In the 2010 growing season, 'UF 4424' and 'Florida Red Ruffles' produced similar amounts of tubers (2.4 kg and 1.9 kg), similar numbers of marketable tubers (44.3 and 40.3), and similar PI (108 and 109).

As shown in Table 1, 'UF 4424' produced fewer marketable tubers than 'UF 4412' in 2009 but produced similar weights and similar number of tubers in 2010.

As shown in Table 1, in tuber grade distribution, the majority (70% or more) of tubers 'UF 4424' produced were in the categories of No. 1, Jumbo, or Mammoth, which was similar to the tuber size distribution of 'Florida Red Ruffles' and 'Florida Sweetheart'.

Table 2 shows a comparison of the plant height, number of leaves, leaf length, and leaf width of 'UF 4424' with 'Florida Sweetheart', 'Florida Red Ruffles', and 'UF 4412' (co-pending application), approximately 4 months from planting 2.54-cm tuber propagules in ground beds in full sun in 2009 and 2010. Values presented are means of two years' data from three replications and three plants measured per plot per year.

TABLE 2

| Cultivar | Plant height (cm) | Leaves (no.) | leaf length (cm) | Leaf width (cm) |
|---|---|---|---|---|
| 'UF 4424' | 28.6 b | 23.3 | 22.9 a | 13.2 b |
| 'Florida Red Ruffles' | 17.9 c | 27.7 | 16.9 b | 10.0 c |
| 'Florida Sweetheart' | 22.9 c | 28.7 | 19.4 b | 13.4 b |

TABLE 2-continued

| Cultivar | Plant height (cm) | Leaves (no.) | leaf length (cm) | Leaf width (cm) |
|---|---|---|---|---|
| 'UF 4412' | 35.7 a[z] | 25.6 | 25.1 a | 15.9 a |
| LSD ($\alpha$ = 0.05) | 3.14 | NS | 2.69 | 1.17 |

[z]mean values with the same letter within columns are not significantly different at P ≤ 0.05.
LSD = least significant difference; NS: not significantly different at P ≤ 0.05.

As shown in Table 2, plants of 'UF 4424' had an average height of 28.6 cm, approximately 7 cm shorter than plants of 'UF 4412'. Leaves of 'UF 4424' had an average size of 22.9 cm by 13.2 cm (length by width), approximately 2.5 cm narrower than leaves of 'UF 4412'. Compared to 'Florida Red Ruffles', plants of 'UF 4424' were about 10 cm taller, leaves of 'UF 4424' were about 6 cm longer and about 3 cm wider. Plants of 'UF 4424' were about 5 cm taller than plants of 'Florida Sweetheart' and leaves of 'UF 4424' were about 3 cm longer than leaves of 'Florida Sweetheart'.

Table 3 shows landscape performance and sunburn tolerance of 'UF 4424' with 'Florida Sweetheart', 'Florida Red Ruffles', and 'UF 4412' when planted in ground beds in full sun in 2009 and 2010. Values presented are means of three replications in each year.

Landscape performance was evaluated on the same plots used for evaluating tuber production. A scale of 1 to 5 was used with 1 being very poor (few leaves and lack of vigor), and 5 being excellent (full plants, numerous leaves, and bright color display). Leaf sun burn tolerance also was evaluated on a scale of 1 to 5, with 1 being very susceptible to sun burns (leaves having numerous sun-damaged areas or holes) and 5 being resistant to sunburn (no visible sun-damaged areas). A total of five evaluations were conducted for plant performance and sunburn tolerance over two growing seasons in August, September, and October 2009, and September and October 2010.

TABLE 3

| | Performance rating | | | | | Sunburn tolerance rating | | | | |
|---|---|---|---|---|---|---|---|---|---|---|
| | 2009 | | | 2010 | | 2009 | | | 2010 | |
| Cultivar | August | September | October | September | October | August | September | October | September | October |
| 'UF 4424' | 4.7 a[z] | 4.8 a | 4.5 a | 4.2 b | 4.2 b | 5.0 a | 4.8 ab | 4.2 b | 4.9 | 4.7 a |
| 'Florida Red Ruffles' | 3.2 b | 3.7 b | 3.5 b | 2.9 c | 3.3 c | 5.0 a | 5.0 a | 4.7 a | 4.6 | 4.2 ab |
| 'Florida Sweetheart' | 4.7 a | 4.5 ab | 3.3 b | 4.7 a | 4.3 b | 4.7 a | 4.5 b | 3.3 c | 4.6 | 3.8 b |

TABLE 3-continued

| | Performance rating | | | | | Sunburn tolerance rating | | | | |
|---|---|---|---|---|---|---|---|---|---|---|
| | 2009 | | | 2010 | | 2009 | | | 2010 | |
| Cultivar | August | September | October | September | October | August | September | October | September | October |
| 'UF 4412' | 4.5 a | 4.8 a | 4.7 a | 4.7 a | 4.9 a | 3.8 b | 4.8 ab | 4.2 b | 4.9 | 4.5 a |
| LSD ($\alpha$ = 0.05) | 1.00 | 1.10 | 0.90 | 0.45 | 0.41 | 0.74 | 0.44 | 0.29 | NS | 0.58 |

[z]mean values with the same letter within columns are not significantly different at P ≤ 0.05.
LSD: least significant differences; NS: Not significantly different at P ≤ 0.05.

As shown in Table 3, plants of 'UF 4424' grown in full sun were full and very attractive and received performance ratings between 4.2 and 4.8. Plants of 'UF 4424' performed significantly better than plants of 'Florida Red Ruffles' in all five evaluations.

As shown in Table 3, plants of 'UF 4424' received a sunburn tolerance score between 4.2 and 5.0, which are similar to those of 'Florida Red Ruffles' (4.2 to 5.0) in four out of five evaluations but are better than those of 'Florida Sweetheart' in two evaluations. These results show that 'UF 4424' possesses excellent sun tolerance.

The suitability of 'UF 4424' for pot plant production was evaluated in 11.4-cm square containers in spring 2012. No. 1 tubers were planted either intact or de-eyed in the commercial potting substrate Fafard 3B Mix (Conrad Fafard Inc., Agawam, Mass.) on 13 Apr. 2012. The greenhouse was covered with a shade cloth and had approximately 35% light exclusion. Average daily temperatures ranged from a low of 17° C. night to 29° C. day during the experiment. The experimental design was a randomized complete block design with eight replications. One teaspoon (approximately seven grams) of Osmocote® controlled fertilizer (15N-2.6P-10K, 5-6 months) was applied to each pot on 13 May. Plant height, plant width, plant quality, number of leaves, and foliar characteristics were recorded on 11 June, approximately 8 weeks after planting. Quality of the potted *Caladium* plants was rated on a scale of 1 to 5, 1=very poor, few leaves, totally unacceptable as potted plants, and 5=very attractive, with many bright, colorful leaves, a full plant, a symmetrical shape, and an appropriate height.

Table 4 shows a comparison of number of days to sprout, plant height, plant width, leaf number, leaf length, leaf width, and quality rating of 'UF 4424' with 'Florida Sweetheart' and 'Florida Red Ruffles' in 2012.

TABLE 4

| | Days to sprout[z] (no.) | | Plant height (cm) | | Plant width (cm) | | Leaves (no.) | | Leaf length (cm) | | Leaf width (cm) | | Quality rating | |
|---|---|---|---|---|---|---|---|---|---|---|---|---|---|---|
| Cultivar | Intact | De-eye | Intact | De-eye | Intact | De-eye | Intact | De-eye | Intact | De-eye | Intact | De-eye | Intact | De-eye |
| 'UF 4424' | 28.4 a[y] | 26.0 a | 24.8 a | 25.0 a | 39.4 | 37.5 | 28.8 | 42.4 b | 17.6 ab | 14.8 | 11.3 b | 9.8 | 3.8 | 4.8 a |
| 'Fla. Red Ruffles' | 21.5 b | 20.5 b | 22.9 ab | 19.3 b | 39.3 | 36.0 | 35.4 | 57.3 a | 16.3 b | 13.0 | 12.1 ab | 8.4 | 3.9 | 4.2 b |
| 'Fla. Sweetheart' | 22.5 b | 25.6 b | 20.5 b | 20.5 b | 39.2 | 35.7 | 31.0 | 51.3 ab | 18.6 a | 14.2 | 12.8 a | 9.4 | 3.9 | 4.6 a |
| LSD ($\alpha$ = 0.05) | 2.22 | 1.77 | 2.71 | 2.43 | NS | NS | NS | 13.86 | 1.39 | NS | 0.96 | NS | NS | 0.27 |

[z]Number of days from planting to the first unfurled leaf.
[y]Mean values within columns that share the same letters are not significantly different at P ≤ 0.05.
NS: Not significantly different at P ≤ 0.05.

As shown in Table 4, when planted intact, tubers of 'UF4424' sprouted ~28 days after planting, approximately 6 to 8 days later than tubers of 'Florida Red Ruffles' and 'Florida Sweetheart'. Plants of 'UF 4424', either intact or de-eyed, were 2 to 5 cm taller than plants of 'Florida Red Ruffles' and 'Florida Sweetheart'. Leaves of 'UF 4424' plants grown in 11.4-cm containers were 1 to 2 cm longer than leaves of 'Florida Red Ruffles'.

As shown in Table 4, with a superb number of bright red, glossy, wavy leaves, pot-grown 'UF4424' plants received high quality ratings (3.8 to 3.9 for intact plants, and 4.2 to 4.8 for de-eyed plants). When tubers were de-eyed, 'UF 4424' produced higher quality pot plants than 'Florida Red Ruffles'.

We claim:

1. A new and distinct *Caladium* plant named 'UF 4424' as illustrated and described herein.

* * * * *